United States Patent [19]

Robson et al.

[11] Patent Number: 4,927,852
[45] Date of Patent: May 22, 1990

[54] INSECTICIDAL COMPOUNDS CHARACTERIZED BY ENHANCED KNOCKDOWN EFFECT

[75] Inventors: Michael J. Robson, Bracknell; Peter J. V. Cleare, Ascot; Mark A. Spinney, Wokingham, all of England

[73] Assignee: Imperial Chemical Industries PLC, London, United Kingdom

[21] Appl. No.: 229,532

[22] Filed: Aug. 8, 1988

[30] Foreign Application Priority Data

Aug. 6, 1987 [GB] United Kingdom ............... 8718620

[51] Int. Cl.$^5$ ................ C07C 69/743; C07C 69/747; C07C 69/74; A01N 53/00
[52] U.S. Cl. ..................................... 514/531; 560/124
[58] Field of Search ....................... 560/124; 514/531

[56] References Cited

U.S. PATENT DOCUMENTS 4,183,950 1/1980 Naumann ............................. 514/531
4,370,346 1/1983 Punja ................................... 514/531

OTHER PUBLICATIONS

Amos, Proc.-Br. Crop Prot. Conf.—Pests Dis. (2), pp. 821–828 (1986).

Primary Examiner—Michael L. Shippen
Attorney, Agent, or Firm—Cushman, Darby & Cushman

[57] ABSTRACT

The invention provides insecticidal compositions exhibiting excellent knockdown activity against public health pests, in particular cockroach species, comprising compounds of formula (I):

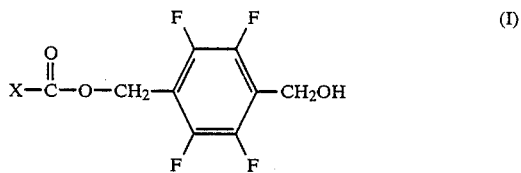

wherein X represents a group of formula:

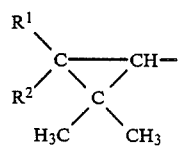

where (i) $R^1$ and $R^2$ are each selected from hydrogen, halo and $C_{1-4}$ alkyl, or (ii) $R^1$ is hydrogen and $R^2$ represents either $R^3(R^4)C=CH-$ or $R^3(R^4)(R^5)C-CH(R^5)-$, where $R^3$ and $R^4$ are selected from hydrogen, methyl, halo and $C_{1-2}$ haloalkyl and $R^5$ is selected from chloro and bromo. The invention also provides methods of use of the compositions, novel compounds of formula (I) and processes for their preparation.

6 Claims, No Drawings

INSECTICIDAL COMPOUNDS CHARACTERIZED BY ENHANCED KNOCKDOWN EFFECT This invention relates to 4-(hydroxymethyl)-2,3,5,6-tetrafluorobenzyl esters useful in combating insects and similar invertebrate pests, to processes for their preparation, to compositions comprising them, and to methods of using them to combat and knock down insects and similar invertebrate pests.

4-(Hydroxymethyl)-2,3,5,6-tetrafluorobenzyl (1RS, cis)-3-(Z-2-chloro-3,3,3-trifluoroprop-1-en-1-yl)-2,2-dimethylcyclopropanecarboxylate has been identified as a metabolite of tefluthrin (4-methyl-2,3,5,6-tetrafluorobenzyl) (1RS, cis)-3-(Z-2-chloro-3,3,3-trifluoroprop-1-en-1-yl)-2,2-dimethylcyclopropanecarboxylate (Amos and Leahey, Proceedings of the British Crop Protection Conference, Pest and Diseases-1986, Volume 2, pages 821-828). We have now found that this and other esters of 4-(hydroxymethyl)-2,3,5,6-tetrafluorobenzyl alcohol, and compositions comprising them, exhibit high levels of contact, residual and fumigant insecticidal activity, characterised by exceptionally high levels of knockdown effect, particularly against cockroach species such as *Blattella germanica*. By knockdown is meant a rapid immobilisation of the affected insect resulting from an induced incapacity for coordinated movement such as flight or walking. This enhanced knockdown effect would not have been suspected from such a close analogue of tefluthrin, which is characterised by a high level of intrinsic activity against soil-dwelling pests, and which does not rely on knockdown for effective control thereof.

Accordingly, in a first aspect, the invention provides an insecticidal composition, comprising an insecticidally effective amount of a compound of formula (I):

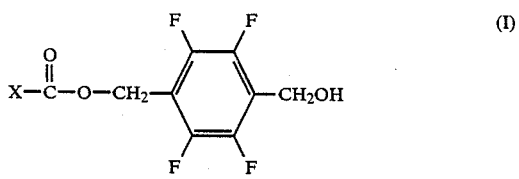

wherein X represents a group of formula:

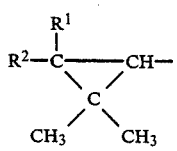

where either (i) $R^1$ and $R^2$ are each selected from hydrogen, halo and alkyl of up to four carbon atoms, or (ii) $R^1$ is hydrogen and $R^2$ represents either a group of formula:

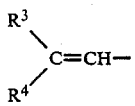

or a group of formula:

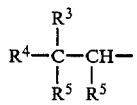

where $R^3$ and $R^4$ are each selected from hydrogen, methyl, halo and haloalkyl of one or two carbon atoms containing at least two fluorine atoms, and $R^5$ is selected from chloro and bromo, or a stereoisomer thereof, in combination with an insecticidally inert carrier or diluent.

In a second aspect, the invention provides a method of combating insect pests at a locus in which an insecticidally effective amount of a composition as hereinbefore described is applied to the locus.

In a third aspect the invention provides a composition for causing knockdown of insect pests comprising an amount of a compound of formula (I), or a stereoisomer thereof, wherein X, $R^1$, $R^2$, $R^3$, $R^4$ and $R^5$ have any of the meanings given hereinbefore, which is effective in causing said knockdown in combination with an insecticidally inert carrier or diluent, and in a fourth aspect, the invention provides a method of combating insect pests at a locus in which an amount of a composition as hereinbefore described which is effective in causing knockdown of insect pests is applied to the locus.

In a further aspect, the invention provides a novel compound of formula (I), or a stereoisomer thereof, wherein X, $R^1$, $R^2$, $R^3$, $R^4$ and $R^5$ have any of the meanings given hereinbefore, with the proviso that X may not represent the group (1RS, cis)-3-(Z-2-chloro-3,3,3-trifluoroprop-1-en-1-yl)-2,2-dimethylcycloprop-1-yl.

The compounds according to formula (I) may exist in a number of stereoisomeric forms resulting from the nature of the group X. Thus, for example, where X represents a substituted cyclopropane group, the carbon atom at the 1-position of the cyclopropane ring may be asymmetrically substituted and may exist in the R-form or the S-form. Similarly the carbon atom at the 3-position of the cyclopropane ring may also exist in the R-form or the S-form when the groups $R^1$ and $R^2$ are not identical; the presence of two such asymmetrically substituted centres in the cyclopropane ring is additionally characterised by the existence of cis and trans isomers, according to the relative configuration of the ring substituents. Where the group $R^2$ contains a carbon-carbon double bond, there exists the further possibility of E- and Z-isomeric forms. Those skilled in the art will recognise that different isomeric forms of the compounds according to formula (I) exhibit different biological characteristics, for example differing levels of insecticidal or knockdown activity. All individual isomeric forms and mixtures thereof, including racemates, arising from stereoisomerism in the group X or elsewhere in the structure of compounds according to formula (I) are within the scope of the invention.

Preferred compounds according to the invention include the (1R) and racemic forms of those listed below:

4-(hydroxymethyl)-2,3,5,6-tetrafluorobenzyl (trans)-3-(Z-2-chloro-3,3,3-trifluoroprop-1-en-1-yl)-2,2-dimethylcyclopropanecarboxylate, 4-(hydroxymethyl)-2,3,5,6-tetrafluorobenzyl (trans)-3-(2,2-dichloroethenyl)-2,2-dimethylcyclopropanecarboxylate, 4-(hydroxymethyl)-2,3,5,6-tetrafluorobenzyl (cis)-3-(2,2-dichloroethenyl)-2,2-dimethylcyclopropanecarboxylate, 4-(hydroxymethyl)-2,3,5,6-tetrafluorobenzyl (trans)-3-(Z-3-bromo-3,3,3-trifluoroprop-1-en-1-yl)-2,2-dimethylcyclopropanecarboxylate, 4-(hydroxymethyl)-2,3,5,6-tetrafluorobenzyl (cis)-3-(Z-2-bromo-3,3,3-trifluoroprop-1-en-1-yl)-2,2-dimethylcyclopropanecarboxylate, 4-(hydroxymethyl)-2,3,5,6-tetrafluorobenzyl (trans)-3-(Z-2,3,3,3-tetrafluoroprop-1-en-1-yl)-2,2-dimethylcyclopropanecarboxylate, 4-(hydroxymethyl)-2,3,5,6-tetrafluorobenzyl (cis)-3-(Z-2,3,3,3-tetrafluoroprop-1-en-1-yl)-2,2-dimethylcyclopropanecarboxylate, 4-(hydroxymethyl)-2,3,5,6-tetrafluorobenzyl (trans)-3-(2,2-dibromoethenyl)-2,2-dimethylcyclopropanecarboxylate, 4-(hydroxymethyl)-2,3,5,6-tetrafluorobenzyl (cis)-3-(2,2-dibromoethenyl)-2,2-dimethylcyclopropanecarboxylate, 4-(hydroxymethyl)-2,3,5,6-tetrafluorobenzyl (trans)-3-(2,2-difluoroethenyl)-2,2-dimethylcyclopropanecarboxylate, 4-(hydroxymethyl)-2,3,5,6-tetrafluorobenzyl (cis)-3-(2,2-difluoroethenyl)-2,2-dimethylcyclopropanecarboxylate, 4-(hydroxymethyl)-2,3,5,6-tetrafluorobenzyl (trans)-3-(E-2-fluoroethenyl)-2,2-dimethylcyclopropanecarboxylate, 4-(hydroxymethyl)-2,3,5,6-tetrafluorobenzyl (cis)-3-(E-2-fluoroethenyl)-2,2-dimethylcyclopropanecarboxylate, 4-(hydroxymethyl)-2,3,5,6-tetrafluorobenzyl (cis)-3-(2-methylprop-1-en-1-yl)-2,2-dimethylcyclopropanecarboxylate, and 4-(hydroxymethyl)-2,3,5,6-tetrafluorobenzyl (trans)-3-(2-methylprop-1-en-1-yl)-2,2-dimethylcyclopropanecarboxylate.

Preferred compounds according to the invention also include:

4-(hydroxymethyl)-2,3,5,6-tetrafluorobenzyl (1R, cis)-3-(Z-2-chloro-3,3,3-trifluoroprop-1-en-1-yl)-2,2-dimethylcyclopropanecarboxylate, and 4-(hydroxymethyl)-2,3,5,6-tetrafluorobenzyl 2,2,3,3-tetramethylcyclopropanecarboxylate.

The compounds of the invention are esters and may be prepared by conventional esterification processes, of which the following are examples:

(a) An acid of formula (II)

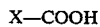     (II)

where X has any of the meanings given hereinabove, may be reacted directly with the alcohol of formula (III):

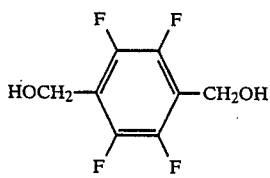     (III)

the reaction preferably taking place in the presence of an acid catalyst, for example, dry hydrogen chloride, or a dehydrating agent, for example, a carbodiimide such as dicyclohexylcarbodiimide.

(b) An acid halide of formula X-COHal where Hal represents a halogen atom, preferably a chlorine atom, and X has any of the meanings given hereinabove, may be reacted with the alcohol of formula (III), the reaction preferably taking place in the presence of a base, for example, pyridine, a trialkylamine, or an alkali metal hydroxide or carbonate.

(c) An acid of formula (II) where X has any of the meanings given hereinabove, or preferably, an alkali metal salt thereof, may be reacted with either (i) a compound of formula (IV):

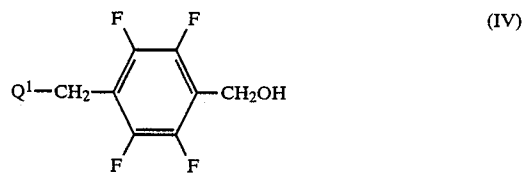     (IV)

where $Q^1$ represents a halogen atom, preferably the bromine or chlorine atom, or with the quaternary ammonium salts derived by reaction of such halides with tertiary amines, for example pyridine or trialkylamines such as triethylamine, or (ii) a compound of formula (IV) wherein $Q^1$ represents the mesylate or tosylate group.

(d) A lower alkyl ester of formula X—COOQ where Q represents a lower alkyl group containing up to six carbon atoms, preferably the methyl or ethyl group, and X has any of the meanings given hereinabove, is heated with the alcohol of formula (III) to effect a transesterification reaction. Preferably the process is performed in the presence of a suitable catalyst, for example, an alkali metal alkoxide such as sodium methoxide, or an alkylated titanium derivative such as tetramethyl titanate or tetraethyl titanate.

All of these conventional processes for the preparation of esters may be carried out using solvents and diluents for the various reactants where appropriate, and may be accelerated or lead to higher yields of product when performed at elevated temperatures or in the presence of appropriate catalysts, for example phase-transfer catalysts. Those skilled in the art will recognise that the alcohol of formula (III) is a diol and that careful control of the processes (a), (b) and (d) is required to minimize its further reaction at the second hydroxyl function; process (c) has been found to be the most suitable for preparation of the compounds of formula (I).

The preparation of individual isomers may be carried out in the same manner but commencing from the corresponding individual isomers of compounds of formula (II). These may be obtained by conventional isomer separation techniques from mixtures of isomers. Thus cis and trans isomers may be separated by fractional crystallisation of the carboxylic acids or salts thereof, whilst the various optically active species may be obtained by fractional crystallisation of salts of the acids with optically active amines, followed by regeneration of the optically pure acid. The optically pure isomeric form of the acid (or its equivalent acid chloride or ester) may then be reacted with the alcohol of formula (III) or a halide, mesylate or tosylate of formula (IV) to produce a compound of formula (I) in the form of an individually pure isomer thereof.

The halides of formula (IV) wherein Hal represents chlorine or bromine may be prepared by monohalogenation of the alcohol of formula (III) according to the process described in UK patent application No. 2153819A. The alcohol of formula (III) may itself be prepared by the processes described in Scheme I.

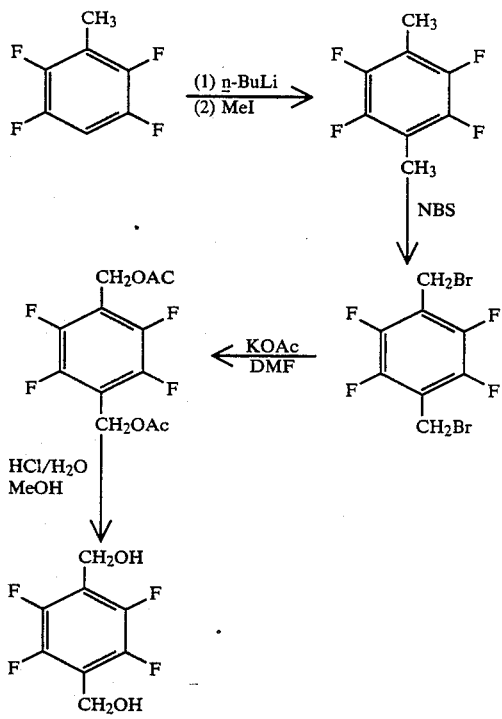

Key:
n-BuLi = n-Butyllithium
NBS = N-bromosuccinimide
DMF = Dimethylformamide
KOAc = Potassium acetate The acids of formula X-COOH from which the esters of formula (I) are derived and processes for their synthesis are well known in the pyrethroid art. Thus, for example, the preparation of 3-(2-fluoroethenyl)-2,2-dimethylcyclopropanecarboxylic acid, and isomers and derivatives thereof, is described by Elliott et al, Pesticide Science, 1986, 17, pages 708–714.

The compounds of formula (I) may be used to combat and control infestations of insect and acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergist, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity for example by increasing the speed of effect, improving kill or knockdown of target insect pests, or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) Pyrethroids such as permethrin, esfenvalerate, deltamethrin, cyhalothrin, biphenthrin, fenpropathrin, cyfluthrin, tefluthrin, empenthrin, fish safe pyrethroids for example ethofenprox, natural pyrethrins, tetramethrin, s-bioallethrin, fenfluthrin, prallethrin, 5-benzyl-3-furylmethyl-(E)-(1R,3S)-2,2-dimethyl-3-(2-oxothiolan-3-ylidenemethyl)cyclopropane carboxylate, and pentafluorobenzyl (cis)-3-[2-fluoro-2-(methoxycarbonyl)ethenyl]-2,2-dimethylcyclopropanecarboxylate.

(b) Organophosphates such as profenofos, sulprofos, dichlorvos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphos-methyl, fenitrothion and diazinon;

(c) Carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) Benzoyl ureas such as triflumuron, chlorofluazuron;

(e) Organic tin compounds such as cyhexatin, fenbutatin oxide, azocyclotin;

(f) Macrolides such as avermectins or milbemycins, for example such as abamectin, avermectin, and milbemycin;

(g) Hormones and synthetic mimics thereof such as juvenile hormone, juvabione, ecdysones, methoprene and hydroprene.

(h) Pheromones.

(i) Organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides or acaricides specific for particular insect species/stages for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylnon, cyromazine, methoprene, chlorfluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as dips, sprays or aerosols. Dips and sprays are generally aqueous dispersions or emulsions of the active ingredient in the presence of one or more known wetting agents, dispersing agents or emulsifying agents (surface active agents). Aerosol compositions may contain the active ingredient or ingredients, a propellant and an inert diluent, for example odourless kerosene or alkylated benzenes. In a preferred form, aerosol compositions may contain from 0.005% to 4% of active ingredient or ingredients, the remainder of the composition comprising a solvent, selected from odourless kerosine and alkylated benzenes, and a propellant. Aerosol compositions may optionally incorporate other additives, for example perfumes or corrosion inhibitors.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and optionally adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 1–99% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of formula (I) and compositions comprising them are very toxic to wide varieties of insect, acarine and other invertebrate pests, including, for example, the following:

*Myzus persicae* (aphids)
*Aphis gossypii* (aphids)
*Aphis fabae* (aphids)
*Megoura viceae* (aphids)
*Aedes aegypti* (mosquitos)
Anopheles spp. (mosquitos)
Culex spp. (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
Aonidiella spp. (scale insects)
Trialeuroides spp. (white flies)
*Bemisia tabaci* (white flies)
*Blattella germanica* (cockroaches)
*Periplaneta americana* (cockroaches)
*Blatta orientalis* (cockroaches)
*Spodoptera littoralis* (cotton leaf worm)
*Heliothis virescens* (tobacco budworms)
*Chortiocetes terminifera* (locusts)
Diabrotica spp. (rootworms)
Agrotis spp. (cutworms)
*Chilo partellus* (maize stem borers)
*Nilaparvata lugens* (plant hoppers)
*Nephotettix cincticeps* (leaf hoppers)
*Panonychus ulmi* (European red mite)
*Panonychus citri* (citrus red mite)
*Tetranychus urticae* (two-spotted spider mite)
*Tetranychus cinnabarinus* (carmine spider mite)

*Phyllocoptruta oleivora* (citrus rust mite)
*Polyphagotarsonemus latus* (broad mite)
Brevipalpus spp. (mites).

The compounds according to formula (I) and compositions comprising them have been shown to be particularly useful in controlling lepidopteran pests of cotton, for example Spodoptera spp. and Heliothis spp. They have also been shown to be particularly useful in combating pests which inhabit the soil, for example Diabrotica spp. They also exhibit exceptionally high levels of knockdown activity against public health pests, and particularly against cockroach species such as *Blattella germanica*. They may also be useful in combating insect and acarine pests which infest domestic animals, such as Lucilia sericata and ixodid tickssuch as Boophilus spp., Ixodes spp., Amblyomma spp., Rhipicephalus spp., and Dermaceutor spp. They are effective in combating both susceptible and resistant strains of these pests in their adult, larval and intermediate stages of growth, and may be applied to the infested host animal by topical, oral or parental administration. The following Examples illustrate various aspects of this invention. In the preparation Examples the products were usually identified and characterised by means of nuclear magnetic reasonance (NMR) spectroscopy and infra red (IR) spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chrompak, CPSil 5CB column of 12.5M length and 0.2 mm internal diameter. Unless otherwise stated, the injection temperature was 100° C., and a temperature gradient of 15° C./minute employed, upto a maximum temperature of 280° C., maintained for 4 minutes. The carrier gas was helium at a column head pressure maintained at 11 psi. Alternative injection and maximum temperatures are indicated in the Examples where appropriate.

$^1$H Nuclear Magnetic Resonance (NMR) spectometry was performed at a frequency of 270 MHz on a Jeol FX 270 NMR spectrometer, unless otherwise indicated. 90 MHz, 60 MHz, 250 MHz and 400 MHz $^1$H NMR spectrometry were performed using Jeol FX 90Q, Brucker WH90, Jeol PMX 60S, Brucker WM250, and Jeol GX400 spectrometers.

$^{19}$F NMR spectrometry was performed on a Jeol FX90Q spectrometer at a frequency of 84.26 MHz. All NMR shift (δ) values are quoted in ppm relative to a standard (TMS or CFCl$_3$). In the NMR data, the following abbreviations are used:
s=singlet
d=doublet
t=triplet
q=quartet
dd=double doublet
m=multiplet
b=broad Molecular Ion (M+) peaks were determined on one of three mass spectrometers: Jeol DX303, Kratos MS80 or Hewlett Packard HP 5992.

EXAMPLE 1

This Example illustrates the preparation of 4-(hydroxymethyl)-2,3,5,6-tetrafluorobenzyl (1RS, cis)-3-(Z-2-chloro-3,3,3-trifluoroprop-1-en-1-yl)-2,2-dimethylcyclopropane carboxylate (Product I).

A mixture of 4-(hydroxymethyl)-2,3,5,6-tetrafluorobenzylbromide (1.3 g, prepared according to the method described in UK patent application No. 2153819A), (1RS, cis)-3-(Z-2-chloro-3,3,3-trifluoroprop-1-en-1-yl)-2,2-dimethylcyclopropanecarboxylic acid (1.5 g), potassium carbonate (1.4 g) and ethylmethylketone (50 cm$^3$) was heated at the reflux temperature for 30 minutes. After cooling, the mixture was poured into water and the products extracted into diethyl ether (2×50 cm$^3$). The combined ethereal extracts were washed with water and dried over anhydrous magnesium sulphate. Evaporation of the solvent under reduced pressure gave an oil which was purified by flash column chromatography on a silica gel support, eluting with dichloromethane, to give the title compound (2.1 g) as a colourless oil.

400 MHz $^1$H NMR (CDCl$_3$): 6.9 (1H, d); 5.23(2H, q); 4.85 (2H, d); 2.2 (2H, t); 1.95(1H, d); 1.30 (6H, s).

EXAMPLE 2

The following compounds were prepared from 4-(hydroxymethyl)-2,3,5,6-tetrafluorobenzyl bromide and the appropriate carboxylic acid by the method of Example 1.

(i)   4-(Hydroxymethyl)-2,3,5,6-tetrafluorobenzyl (1RS, trans)-3-(Z-2-chloro-3,3,3-trifluoroprop-1-en-1-yl)-2,2-dimethylcyclopropanecarboxylate (Product II)

$^1$H NMR (CDCl$_3$): 6.14 (1H, d); 5.26 (2H, s); 4.85 (2H, s); 2.44 (1H, dd); 2.06 (1H, b); 1.78 (1H, d); 1.35 (3H, s);

Infra Red: 3300, 1730 cm$^{-1}$.

(ii)  4-(Hydroxymethyl)-2,3,5,6-tetrafluorobenzyl (1RS, trans)-3-(Z-2-bromo-3,3,3-trifluoroprop-1-en-1-yl)-2,2-dimethylcyclopropanecarboxylate (Product III).

$^1$H NMR (CDCl$_3$): 6.36 (1H, d); 5.2 (2H, s); 4.84 (2H, d); 2.36 (1H, m); 2.06 (1H, t); 1.78 (1H, d); 1.34 (3H, s); 1.24 (3H, s).

Infra Red: 3300, 1730 cm$^{-1}$.

Melting point: 109°–110° C.

(iii) 4-(Hydroxymethyl)-2,3,5,6-tetrafluorobenzyl (1RS, cis)-3-(Z-2,3,3,3-tetrafluoroprop-1-en-1-yl)-2,2-dimethylcyclopropanecarboxylate (Product IV).

90 MHz $^1$H NMR (CDCl$_3$): 6.21, 5.84 (1H, 2d); 5.22 (2H, s); 4.84 (2H, d); 1.8–2.3 (3H, m); 1.3 (6H, 2).

$^{19}$F NMR (CDCl$_3$): −138.2(m); −143.2(q); −145.2(q).

Infra Red: 3300, 1730 cm$^{-1}$.

(iv)  4-(Hydroxymethyl)-2,3,5,6-tetrafluorobenzyl (1RS, trans)-3-(Z-2,3,3,3-tetrafluoroprop-1-en-1-yl)-2,2-dimethylcyclopropanecarboxylate (Product V).

90 MHz $^1$H NMR (CDCl$_3$): 5.45 and 5.10 (1H, 2d); 5.25 (2H, t); 4.84 (2H, s); 2.35 (1H, 2d); 2.0 (1H, b); 1.70 (1H, d); 1.34 (3H, s); 1.24 (3H, s).

$^{19}$F NMR (CDCl$_3$): −136.0 (2q); −143.1 (q); −145.2 (q).

(v)   4-(Hydroxymethyl)-2,3,5,6-tetrafluorobenzyl 2,2,3,3-tetramethylcyclopropanecarboxylate (Product VI).

Infra Red: 3300, 1730 cm$^{-1}$.

(vi)  4-(Hydroxymethyl)-2,3,5,6-tetrafluorobenzyl (1RS, trans)-3-(2,2-dichloroethenyl)-2,2-dimethylcyclopropanecarboxylate (Product VII).

$^1$H NMR (CDCl$_3$): 5.61 (1H, d); 5.25 (2H, s); 4.85 (2H, s); 2.28 (1H, dd); 2.04 (1H, b); 1.61 (1H, d); 1.30 (3H, s).

Infra Red: 3300, 1730 cm$^{-1}$.
Melting Point: 86°–88° C.

(vii) 4-(Hydroxymethyl)-2,3,5,6-tetrafluorobenzyl (1RS, cis/trans)-3-(2,2-difluoroethenyl)-2,2-dimethylcyclopropanecarboxylate, cis:trans ratio 1:9, (Product VIII).

$^1$H NMR (CDCl$_3$): 5.24 (s, 2H); 4.84 (s, 2H); 4.08–3.95 (dd, 1H); 2.0 (t, 2H); 1.44 (d, 1H); 1.26 (s, 3H); 1.14 (s, 3H).

(viii) 4-(Hydroxymethyl)-2,3,5,6-tetrafluorobenzyl (1RS, cis/trans)-3-(2-methylprop-1-en-1-yl)-2,2-dimethylcyclopropanecarboxylate, cis:trans ratio 2:3, (Product IX).

400 MHz $^1$H NMR (CDCl$_3$): 5.35–5.14 (m, 2.5H); 4.8–4.9 (m, 2.5H); 2.1–1.95 (3t, 2H); 1.78–1.64 (m, 6H); 1.3–1.15 (dd, 6H).

EXAMPLE 3

This Example illustrates the preparation of 4-(Hydroxymethyl)-2,3,5,6-tetrafluorobenzyl (1RS, trans)-3-(E-2-fluoroethenyl)-2,2-dimethylcyclopropanecarboxylate (Product X).

A stirred suspension of (1RS, trans)-3-(EZ-2-fluoroethenyl)-2,2-dimethylcyclopropanecarboxylic acid (0.046 g), 4-(bromomethyl)-2,3,5,6-tetrafluorobenzyl alcohol (0.07 g) and potassium carbonate (0.042 g) in methyl ethyl ketone (3 cm$^3$) was heated at the reflux temperature for 3 hours, then cooled to the ambient temperature (ca. 22° C.) and stood for 17 hours. The mixture was diluted with diethyl ether and filtered through Hyflo. The diluted filtrate was concentrated by evaporation under reduced pressure to give an oil (0.06 g), which was purified by flash column chromatography on a silica gel support, eluting with a 1:1 mixture by volume of hexane and diethyl ether. The component having an Rf value of ca. 0.5 by TLC on silica gel (same solvent system) was collected and isolated by evaporation of the eluent, and further purified by semi-preparative HPLC, eluting with a 4:1 mixture by volume of hexane and diethyl ether. The second fraction collected was identified as 4-hydroxymethyl-2,3,5,6-tetrafluorobenzyl (1RS, trans)-3-(E-2-fluoroethenyl)-2,2-dimethylcyclopropanecarboxylate (0.023 g); the first fraction (not isolated) was believed to consist mainly of the corresponding Z-isomer.

$^1$H NMR (CDCl$_3$): 6.76, 6.48 (d, 1H); 5.32–5.12 (m, 3H); 4.84 (s, 2H); 2.2–2.1 (b, 1H); 1.9 (dd, 1H); 1.48 (d, 1H); 1.25 (s, 3H); 1.14 (s, 3H).

EXAMPLE 4

This Example illustrates the composition of typical preparations, or concentrates therefor, which may be used for the application of the compounds according to the invention when used for the control of insect pests. The high level of knockdown activity of the compounds of the invention renders them particularly suitable for admixture with known killing agents for the purposes of providing a preparation which causes rapid knockdown followed by kill of the target pest. As the compounds according to the invention themselves exhibit a lethal effect, admixture with other killing agents is optional.

Examples of killing agents which may be used in the following examples include, but are not limited to, permethrin, cypermethrin, cyhalothrin, lambda-cyhalothrin and pirimiphos-methyl.

| (i) Aerosol concentrate: | % Weight |
|---|---|
| Compound No. II | 10 |
| Optional killing agent | 30 |
| Alkylated benzene solvent (e.g. SOLVESSO 100) | to 100% |

| (ii) Aerosol: | % Weight |
|---|---|
| Aerosol concentrate (as in (i) above | 1 |
| Odourless kerosene | 25 |
| Liquid propane gas propellant (e.g. CALOR 48) | 62 |
| Methylene dichloride | 12 |

| (iii) Ready for use formulation: | % Weight |
|---|---|
| Aerosol concentrate (as in (i) above | 1 |
| Odourless kerosene | 99 |

| (iv) Hot/cold fogging concentrate: | % Weight |
|---|---|
| Product IV | 10 |
| Optional killing agent | 25 |
| Alkylated benzene solvent (e.g. SOLVESSO 200) | 50 |
| Paraffinic solvent (e.g. EXSOL D200/240) | to 100% |

| (v) Oil/water dilutable ultra low volume (ULV) formulation: | % Weight |
|---|---|
| Product I | 3 |
| Optional killing agent | 10 |
| Calcium dodecylbenzene-sulphonate (e.g. CALX) | 3 |
| Nonylphenol ethoxylate/propoxylate (e.g. SYNPERONIC NPE1800) | 4.5 |
| Alkylated benzene solvent (e.g. SOLVESSO 200) | 40 |
| Paraffinic solvent (e.g. EXSOL D200/240) | to 100% |

| (vi) Oil dilutable ultra volume (ULV) formulation: | % Weight |
|---|---|
| Product IX | 3 |
| Optional killing agent | 10 |
| Alkylated benzene solvent (e.g. SOLVESSO 200) | 50 |
| Paraffinic solvent (e.g. EXSOL D200/240) | to 100% |

Note:
SOLVESSO, CALOR, EXSOL, CALX and SYNPERONIC are registered trademarks.

EXAMPLE 5

This Example illustrates the insecticidal properties of the Products of this invention.

The activity of the Product was determined using a variety of insect pests. The Product was used in the form of liquid preparations containing 500, 250 or 100 parts per million (ppm) by weight of the Product. The preparations were made by dissolving the Product in acetone and diluting the solutions with water containing 0.01% by weight of a wetting agent sold under the trade name "SYNPERONIC" NX until the liquid preparations contained the required concentration of the Product. "SYNPERONIC" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at periods usually varying from one to three days after the treatment.

The results of the tests are given in Table II for each of the Products, at the rate in parts per million given in the second column as a grading of mortality designated as A, B or C wherein A indicates 80–100% mortality, B indicates 50–79% mortality and C indicates less than 50% mortality.

In Table II the pest organism used is designated by a letter code and the pests species, the support medium or food, and the type and duration of test is given in Table I.

EXAMPLE 6

This Example illustrates the knockdown activity of the compounds according to the invention.

*Blattella germanica* knockdown test

The test compound was dissolved in acetone (2 cm$^3$) and the solution diluted to the required concentration with kerosene. 1 cm$^3$ of this preparation was sprayed directly onto 10 *Blattella germanica* (adult males) held in a netted plastic pot in a Burkhard Potter Tower. Assessment of knockdown was performed at intervals of 5 minutes up to a total of 20 minutes. On removal from the Burkhard Potter Tower, the insects were held at 25° C. and 65% relative humidity for 48 hours, and an assessment of mortality performed. Each test was repeated at least once. Results are given in Table III. Results for a similar test in which the knockdown efficacy of tefluthrin was determined are given in Table IV.

In some tests, additional knockdown assessment was performed at intervals of 1, 2, 3 and 4 minutes, and $KT_{50}$ and $KT_{90}$ values determined (the time taken, in minutes, to knockdown 50% and 90% respectively of the test insects).

TABLE I

| CODE LETTERS (TABLE IV) | TEST SPECIES | SUPPORT MEDIUM/FOOD | TYPE OF TEST | DURATION (days) |
|---|---|---|---|---|
| TUa | *Tetranychus urticae* (spider mites - adult) | French bean leaf | Contact | 3 |
| MP | *Myzus persicae* (aphids) | Chinese Cabbage leaf | Contact | 3 |
| NC | *Nephotettix cincticeps* (green leaf hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| SP | *Spodoptera exigua* (lesser army worm - larvae) | Cotton leaf | Residual | 3 |

"Contact" test indicates that both pests and medium were treated and "resiudal" indicates that the medium was treated before infestation with the pests.

TABLE II

| PRODUCT | EXAMPLE NO. | RATE (ppm) | Tua | MP | NC | HV | DB | BG | MD | SP |
|---|---|---|---|---|---|---|---|---|---|---|
| I | 1 | 500 | A | A | A* | A | A | A | B | A |
| II | 2(i) | 100 | B | A | A | A | A | C | B | A |
| III | 2(ii) | 100 | C | A | A | C | A | A | C | A |
| IV | 2(iii) | 100 | A | A | A | A | A | A | A | A |
| V | 2(iv) | 100 | C | A | A | A | A | B | A | A |
| VI | 2(v) | 100 | B | C | A | C | B | C | C | B |
| VII | 2(vi) | 500 | C | A | A | B | A | B | B | A |
| VIII | 2(vii) | 100 | C | C | B+ | B+ | C+ | C | C** | C+ |
| IX | 2(viii) | 100 | C | A | A+ | A+ | A+ | A | A** | A+ |

*Nephotettix cincticeps replaced by Nilaparvata lugens in this test.
+Test duration of 2 days.
** Test duration of 3 days.

TABLE III

| TEST COMPOUND | APPLICATION RATE (ppm) | TEST | % Knockdown Observed | | | | % Mortality 48 hrs | $KT_{50}$ min | $KT_{90}$ min |
|---|---|---|---|---|---|---|---|---|---|
| | | | 5 min | 10 min | 15 min | 20 min | | | |
| I | 250 | 1 | 100 | | | | 100 | | |
| | | 2 | 100 | | | | 100 | | |
| II | 250 | 1 | 100 | | | | 90 | | |
| | | 2 | 100 | | | | 100 | | |

TABLE III-continued

| TEST COMPOUND | APPLICATION RATE (ppm) | TEST | % Knockdown Observed | | | | % Mortality 48 hrs | $KT_{50}$ min | $KT_{90}$ min |
|---|---|---|---|---|---|---|---|---|---|
| | | | 5 min | 10 min | 15 min | 20 min | | | |
| III | 250 | 1 | 100 | | | | 100 | | |
| | | 2 | 100 | | | | 60 | | |
| IV | 250 | 1 | 100 | | | | 100 | | |
| | | 2 | 100 | | | | 100 | | |
| V | 250 | 1 | 100 | | | | 100 | | |
| | | 2 | 100 | | | | 100 | | |
| VI | 250 | 1 | 100 | | | | 100 | | |
| | | 2 | 100 | | | | 100 | | |
| VIII+ | 625 | 1 | 100 | | | | 100 | 0.28 | 0.45 |
| | | 2 | 100 | | | | 100 | | |
| | | 3 | 100 | | | | 100 | | |
| IX+ | 625 | 1 | 100 | | | | 100 | 0.23 | 0.50 |
| | | 2 | 100 | | | | 100 | | |
| | | 3 | 100 | | | | 100 | | |
| X | 250 | 1 | 100 | | | | 70 | 1.9 | 2.7 |
| | | 2 | 100 | | | | 100 | | |
| Tetramethrin | 250 | * | 80 | 100 | | | 50 | 1.7 | 3.2 |

+Synergised with piperonyl butoxide.
*Meaned values from 24 observations.

TABLE IV

| TEST COMPOUND | APPLICATION RATE (ppm) | TEST | % Knockdown Observed | | | | % Mortality 48 hrs | $KT_{50}$ min | $KT_{90}$ min |
|---|---|---|---|---|---|---|---|---|---|
| | | | 5 min | 10 min | 15 min | 20 min | | | |
| Tefluthrin | 250 | 1 | 0 | 90 | 100 | | 100 | 7.8 | 10.6 |
| | | 2 | 10 | 100 | | | 100 | | |
| | | 3 | 10 | 80 | 100 | | 100 | | |
| Tetramethrin | 250 | 1 | 100 | | | | 80 | 2.0 | 3.1 |
| | | 2 | 100 | | | | 90 | | |
| | | 3 | 100 | | | | 50 | | |

We claim:

1. An insecticidal composition, comprising an insecticidally effective amount of a compound of formula (I):

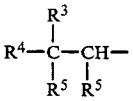

wherein X represents a group of formula:

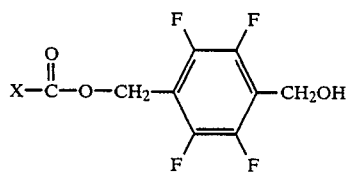

where either (i) $R^1$ and $R^2$ are each selected from hydrogen, halo and alkyl of up to four carbon atoms, or (ii) $R^1$ is hydrogen and $R^2$ represents either a group of formula:

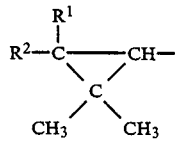

or a group of formula:

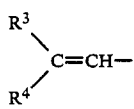

where $R^3$ and $R^4$ are each selected from hydrogen, methyl, halo and haloalkyl of one or two carbon atoms containing at least two fluorine atoms, and $R^5$ is selected from chloro and bromo, or a stereoisomer thereof, in combination with an insecticidally inert carrier or diluent.

2. A method of combating insect pests at a locus in which an insecticidally effective amount of a composition as claimed in claim 1 is applied to the locus.

3. A method of combating insect pests at a locus in which an amount of a composition as according to claim 1 which is effective in causing knockdown of insect pests is applied to the locus.

4. A composition according to claim 1 adapted for application by aerosol.

5. A compound of formula (I):

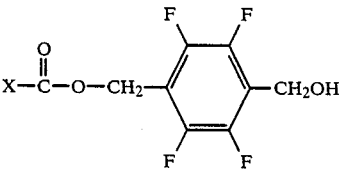

or a stereoisomer thereof, wherein X represents a group of formula:

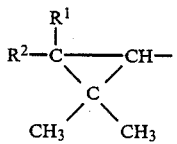

and either (i) $R^1$ and $R^2$ are each selected from hydrogen, halo and alkyl of up to four carbon atoms, or (ii) $R^1$ is hydrogen and $R^2$ represents either a group of formula:

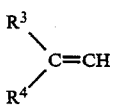

or a group of formula:

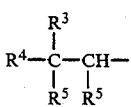

where $R^3$ and $R^4$ are each selected from hydrogen, methyl, halo, and haloalkyl of one or two carbon atoms containing at least two fluorine atoms, and $R^5$ is selected from chloro and bromo; with the proviso that X may not represent the group (1RS, cis)-3-(Z-2-chloro-3,3,3-trifluoroprop-1-en-1-yl)-2,2-dimethylcycloprop-1-yl, the group (1R, cis)-3-(Z-2-chloro-3,3,3-trifluoroprop-1-en-1-yl)-2,2-dimethylcycloprop-1-yl, or the group (1S, cis)-3-(Z-2-chloro-3,3,3-trifluoroprop-1-en-1-yl)-2,2-dimethylcycloprop-1-yl.

6. A compound according to claim 5 which is selected from the group of compounds consisting of:

4-(hydroxymethyl)-2,3,5,6-tetrafluorobenzyl (1R, trans)-3-(Z-2-chloro-3,3,3-trifluoroprop-1-en-1-yl)-2,2-dimethylcyclopropanecarboxylate;

4-(hydroxymethyl)-2,3,5,6-tetrafluorobenzyl (1RS, trans)-3-(Z-2-chloro-3,3,3-trifluoroprop-1-en-1-yl)-2,2-dimethylcyclopropanecarboxylate;

4-(hydroxymethyl)-2,3,5,6-tetrafluorobenzyl (1R, trans)-3-(2,2-dichloroethenyl)-2,2-dimethylcyclopropanecarboxylate;

4-(hydroxymethyl)-2,3,5,6-tetrafluorobenzyl (1RS, trans)-3-(2,2-dichloroethenyl)-2,2-dimethylcyclopropanecarboxylate;

4-(hydroxymethyl)-2,3,5,6-tetrafluorobenzyl (1R, cis)-3-(2,2-dichloroethenyl)-2,2-dimethylcyclopropanecarboxylate;

4-(hydroxymethyl)-2,3,5,6-tetrafluorobenzyl (1RS, cis)-3-(2,2-dichloroethenyl)-2,2-dimethylcyclopropanecarboxylate;

4-(hydroxymethyl)-2,3,5,6-tetrafluorobenzyl (1R, trans)-3-(Z-2-bromo-3,3,3-trifluoroprop-1-en-1-yl)-2,2-dimethylcyclopropanecarboxylate;

4-(hydroxymethyl)-2,3,5,6-tetrafluorobenzyl (1RS, trans)-3-(Z-2-bromo-3,3,3-trifluoroprop-1-en-1-yl)-2,2-dimethylcyclopropanecarboxylate;

4-(hydroxymethyl)-2,3,5,6-tetrafluorobenzyl (1R, cis)-3-(Z-2-bromo-3,3,3-trifluoroprop-1-en-1-yl)-2,2-dimethylcyclopropanecarboxylate;

4-(hydroxymethyl)-2,3,5,6-tetrafluorobenzyl (1RS, cis)-3-(Z-2-bromo-3,3,3-trifluoroprop-1-en-1-yl)-2,2-dimethylcyclopropanecarboxylate;

4-(hydroxymethyl)-2,3,5,6-tetrafluorobenzyl (1R, trans)-3-(Z-2,3,3,3-tetrafluoroprop-1-en-1-yl)-2,2-dimethylcyclopropanecarboxylate;

4-(hydroxymethyl)-2,3,5,6-tetrafluorobenzyl (1RS, trans)-3-(Z-2,3,3,3-tetrafluoroprop-1-en-1-yl)-2,2-dimethylcyclopropanecarboxylate;

4-(hydroxymethyl)-2,3,5,6-tetrafluorobenzyl (1R, cis)-3-(Z-2,3,3,3-tetrafluoroprop-1-en-1-yl)-2,2-dimethylcyclopropanecarboxylate;

4-(hydroxymethyl)-2,3,5,6-tetrafluorobenzyl (1RS, cis)-3-(Z-2,3,3,3-tetrafluoroprop-1-en-1-yl)-2,2-dimethylcyclopropanecarboxylate;

4-(hydroxymethyl)-2,3,5,6-tetrafluorobenzyl (1R, trans)-3-(2,2-dibromoethenyl)-2,2-dimethylcyclopropanecarboxylate;

4-(hydroxymethyl)-2,3,5,6-tetrafluorobenzyl (1RS, trans)-3-(2,2-dibromoethenyl)-2,2-dimethylcyclopropanecarboxylate;

4-(hydroxymethyl)-2,3,5,6-tetrafluorobenzyl (1R, cis)-3-(2,2-dibromoethenyl)-2,2-dimethylcyclopropanecarboxylate;

4-(hydroxymethyl)-2,3,5,6-tetrafluorobenzyl (1RS, cis)-3-(2,2-dibromoethenyl)-2,2-dimethylcyclopropanecarboxylate;

4-(hydroxymethyl)-2,3,5,6-tetrafluorobenzyl (1R, trans)-3-(2,2-difluoroethenyl)-2,2-dimethylcyclopropanecarboxylate;

4-(hydroxymethyl)-2,3,5,6-tetrafluorobenzyl (1RS, trans)-3-(2,2-difluoroethenyl)-2,2-dimethylcyclopropanecarboxylate;

4-(hydroxymethyl)-2,3,5,6-tetrafluorobenzyl (1R, cis)-3-(2,2-difluoroethenyl)-2,2-dimethylcyclopropanecarboxylate;

4-(hydroxymethyl)-2,3,5,6-tetrafluorobenzyl (1RS, cis)-3-(2,2-difluoroethenyl)-2,2-dimethylcyclopropanecarboxylate;

4-(hydroxymethyl)-2,3,5,6-tetrafluorobenzyl (1R, trans)-3-(E-2-fluoroethenyl)-2,2-dimethylcyclopropanecarboxylate;

4-(hydroxymethyl)-2,3,5,6-tetrafluorobenzyl (1RS, trans)-3-(E-2-fluoroethenyl)-2,2-dimethylcyclopropanecarboxylate;

4-(hydroxymethyl)-2,3,5,6-tetrafluorobenzyl (1R, cis)-3-(E-2-fluoroethenyl)-2,2-dimethylcyclopropanecarboxylate;

4-(hydroxymethyl)-2,3,5,6-tetrafluorobenzyl (1RS, cis)-3-(E-2-fluoroethenyl)-2,2-dimethylcyclopropanecarboxylate;

4-(hydroxymethyl)-2,3,5,6-tetrafluorobenzyl (1R, trans)-3-(2-methylprop-1-en-1-yl)-2,2-dimethylcyclopropanecarboxylate;

4-(hydroxymethyl)-2,3,5,6-tetrafluorobenzyl (1RS, trans)-3-(2-methylprop-1-en-1-yl)-2,2-dimethylcyclopropanecarboxylate;

4-(hydroxymethyl)-2,3,5,6-tetrafluorobenzyl (1R, cis)-3-(2-methylprop-1-en-1-yl)-2,2-dimethylcyclopropanecarboxylate;

4-(hydroxymethyl)-2,3,5,6-tetrafluorobenzyl (1RS, cis)-3-(2-methylprop-1-en-1-yl)-2,2-dimethylcyclopropanecarboxylate;

4-(hydroxymethyl)-2,3,5,6-tetrafluorobenzyl 2,2,3,3-tetramethylcyclopropanecarboxylate.

* * * * *